United States Patent [19]

Hahn et al.

[11] Patent Number: 5,051,504
[45] Date of Patent: Sep. 24, 1991

[54] DOUBLED TRIPHENYLMETHANE DYES HAVING BIS ACYLPIPERAZINE LINKAGE

[75] Inventors: Erwin Hahn, Heidelberg; Walter Breitschaft, Mannheim; Udo Mayer, Frankenthal; Gunter-Rudolf Schroeder, Ludwigshafen, all of Fed. Rep. of Germany

[73] Assignee: BASF Aktiengesellschaft, Ludwigshafen, Fed. Rep. of Germany

[21] Appl. No.: 521,382

[22] Filed: May 10, 1990

[30] Foreign Application Priority Data

May 31, 1989 [DE] Fed. Rep. of Germany ....... 3917601

[51] Int. Cl.$^5$ ..................... C09B 11/20; D21H 21/28
[52] U.S. Cl. .................... 544/58.6; 544/58.7; 544/82; 544/121; 544/357; 544/360; 544/387
[58] Field of Search ............ 544/387, 58.6, 58.7, 544/82, 121, 357, 360

[56] References Cited

U.S. PATENT DOCUMENTS

| | | | |
|---|---|---|---|
| 3,347,860 | 10/1967 | Irikura et al. | 544/387 |
| 3,763,166 | 10/1973 | Dexter et al. | 544/387 |
| 3,828,071 | 8/1974 | Kast et al. | 548/511 |
| 4,000,135 | 12/1976 | Kast et al. | 544/357 X |
| 4,223,144 | 9/1980 | Kast et al. | 544/392 |
| 4,340,540 | 7/1982 | Hermann | 544/372 X |

FOREIGN PATENT DOCUMENTS

| | | | |
|---|---|---|---|
| 1481016 | 4/1967 | France | 544/387 |
| 460020 | 9/1968 | Switzerland | 544/387 |

OTHER PUBLICATIONS

Kast et al., Chemical Abstracts, vol. 91, #6408q (1979).
Irikura et al., J. Med. Chem., vol. II, pp. 801 to 804 (1968).

*Primary Examiner*—Mary C. Lee
*Assistant Examiner*—Fiona T. Powers
*Attorney, Agent, or Firm*—Oblon, Spivak, McClelland, Maier & Neustadt

[57] ABSTRACT

Triphenylmethane dyes of the formula

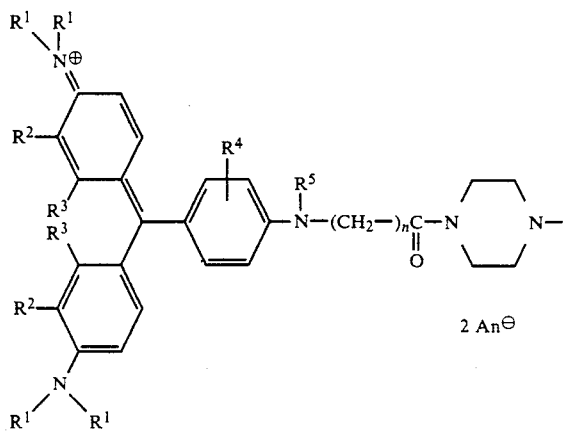

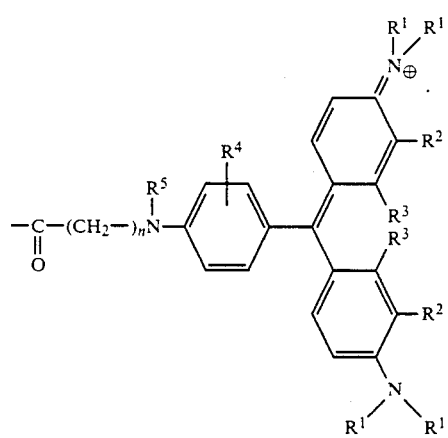

where each
$R^1$ is independently of the others hydrogen or substituted or unsubstituted $C_1$–$C_6$-alkyl, or two $R^1$ radicals together with the nitrogen atom joining them form a heterocyclic radical,
$R^2$ and $R^5$ is independently of the others hydrogen or $C_1$–$C_4$-alkyl,
$R^3$ and $R^4$ is independently of the others hydrogen, $C_1$–$C_4$-alkyl, $C_1$–$C_4$-alkoxy or halogen,
An$^\ominus$ is one equivalent of an anion, and
n is 1 or 2,
preparable from piperazine derivatives as intermediates, are useful for coloring paper.

2 Claims, No Drawings

DOUBLED TRIPHENYLMETHANE DYES HAVING BIS ACYLPIPERAZINE LINKAGE

The present invention relates to novel triphenylmethane dyes of the formula I $$\text{[Structure of formula I: two triphenylmethane dye units linked via } -N(R^5)-(CH_2)_n-C(=O)-N\text{-piperazine-}N-C(=O)-(CH_2)_n-N(R^5)-\text{ bridge, with 2An}^{\ominus}\text{ counter ions]}$$

where each $R^1$ is identical or different being independently of the others hydrogen or substituted or unsubstituted $C_1$–$C_6$-alkyl, or two R radicals together with the nitrogen atom joining them form a saturated 5- or 6-membered heterocyclic radical which may contain further hetero atoms, $R^2$ and $R^5$ is identical or different, being independently of the others hydrogen or $C_1$–$C_4$-alkyl, $R^3$ and $R^4$ is identical or different, being independently of the others hydrogen, $C_1$–$C_4$-alkyl, $C_1$–$C_4$-alkoxy or halogen, $An^{\ominus}$ is one equivalent of an anion, and n is identical or different, being 1 or 2, and also to piperazine derivatives as intermediates therefor.

DE-A-2 739 953 already discloses doubled triphenylmethane dyes, for example with a p-xylylene or 1,4-piperazinediyl bridge member. To prepare those dyes which have a p-xylylene bridge it is necessary to start from 1,4-bis(chloromethyl)benzene, which is difficult to handle. Those dyes with a 1,4-piperazinediyl bridge still have deficient application properties.

It is an object of the present invention to provide new doubled triphenylmethane dyes which are preparable by means of simple intermediates and which have favorable application properties.

We have found that this object is achieved by the triphenylmethane dyes of the formula I defined at the beginning.

If $R^1$ is substituted $C_1$–$C_6$-alkyl, possible substituents are, for example, hydroxyl, $C_1$–$C_4$-alkoxy, $C_1$–$C_4$-alkanoyloxy, $C_1$–$C_4$-alkoxycarbonyl, cyano, chlorine, acetyl, acetylamino or phenyl.

$R^1$, $R^2$, $R^3$, $R^4$ and $R^5$ are each for example methyl, ethyl, propyl, isopropyl, butyl, isobutyl, sec-butyl or tert-butyl.

$R^3$ and $R^4$ are each further for example methoxy, ethoxy, propoxy, isopropoxy, butoxy, isobutoxy, sec-butoxy, fluorine, chlorine or bromine.

$R^1$ is further for example pentyl, isopentyl, neopentyl, tert-pentyl, hexyl, 2-methylpentyl, 2-hydroxyethyl, 2- or 3-hydroxypropyl, 2-methoxyethyl, 2-ethoxyethyl, 2- or 3-methoxypropyl, 2- or 3-ethoxypropyl, 2-formyloxyethyl, 2-acetyloxyethyl, 2- or 3-formyloxypropyl, 2- or 3-acetyloxypropyl, 2-methoxycarbonylethyl, 2-ethoxycarbonylethyl, 2- or 3-methoxycarbonylpropyl, 2- or 3-ethoxycarbonylpropyl, 2-cyanoethyl, 2- or 3-cyanopropyl, 2-chloroethyl, 2- or 3-chloropropyl, but-3-on-1yl, pent-4-on-1-yl, 2-methylbut-3-on-1-yl, 2-acetylaminoethyl, 2- or 3-acetylaminopropyl, benzyl or 1- or 2-phenylethyl.

If two $R^1$ radicals together with the nitrogen atom joining them form a saturated 5- or 6-membered heterocyclic radical which may contain further hetero atoms, such radicals can be for example pyrrolidino, piperidino, morpholino, thiomorpholino, piperazino and N-($C_1$–$C_4$-alkyl)piperazino, such as N-methyl- or N-ethylpiperazino.

Suitable anions from which to derive the anion equivalent $An^{\ominus}$ are for example halides, such as fluoride, chloride, bromide or iodide, hydrogensulfate, sulfat, hydrogenphosphate, phosphate, borate, tetrafluoroborate, trichlorozincate, methosulfate, ethosulfat, benzenesulfonate, o- or p-toluenesulfonate, methanesulfonate, formate, acetate, propionate, hydroxyacetate, methoxyacetate and lactate.

Preference is given to triphenylmethane dyes of the formula I where each of $R^1$ is independently of the others hydrogen, $C_1$–$C_4$-alkyl 2-hydroxyethyl, $R^2$ is independently of the others hydrogen or methyl, $R^3$ and $R^4$ is independently of the others hydrogen, methyl, methoxy, ethoxy or halogen, and $R^5$ is independently of the other hydrogen or $C_1$–$C_4$-alkyl, and $An^{\ominus}$ and n are each as defined above.

Particular preference is given to triphenylmethane dyes of the formula I where each n is 1.

It is worth mentioning in particular triphenylmethane dyes of the formula I where each $R^1$ is independently of the others hydrogen, methyl or ethyl, $R^2$ is independently of the others hydrogen or methyl, $R^3$ is independently of the others hydrogen or methoxy, $R^4$ is independently of the other hydrogen, methyl, methoxy or chlorine, $R^5$ is independently of the other hydrogen, methyl or ethyl, n is 1 and $An^{\ominus}$ is as defined above.

The triphenylmethane dyes of the formula I according to the present invention can be prepared in a conventional manner. For example, a piperazine derivative of the formula III

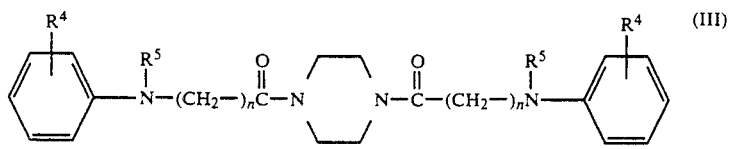

where $R^4$, $R^5$ and n are each as defined above, can be linked to a diphenylmethane of the formula IV

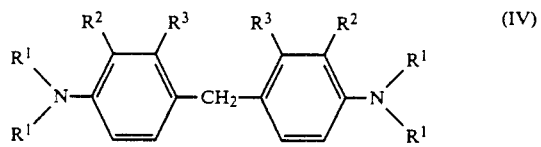

where $R^1$, $R^2$ and $R^3$ are each as defined above, by a catalytic oxidation reaction. Such catalytic oxidation reactions form part of the state of the art and are described for example in US-A-3 828 071 and US-A-4 000 135.

It is also possible, for example, to condense a piperazine derivative of the formula III with a benzophenone of the formula V

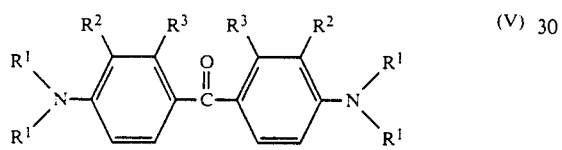

where $R^1$, $R^2$ and $R^3$ are each as defined above, in a conventional manner.

It is a further object of the present invention to provide new piperazine derivatives which are advantageously used as intermediates for the synthesis of triphenylmethane dyes of the formula I.

We have found that this object is achieved by the piperazine derivatives of the formula II Med. Chem. 11 (1968), 801–804, as drugs having an analgesic effect. Their possible suitability for use as intermediates for the synthesis of triphenylmethane dyes is not mentioned therein.

The piperazine derivatives of the formula II according to the present invention can be obtained for example by the method described in J. Med. Chem. (loc. cit.) from acylpiperazines of the formula VI

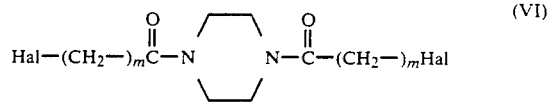

where Hal is halogen and m is as defined above, by reaction with anilines of the formula VII

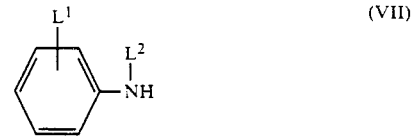

where $L^1$ and $L^2$ are each as defined above.

The novel piperazine derivatives of the formula II are useful intermediates for preparing triphenylmethane dyes of the formula I.

The novel triphenylmethane dyes of the formula I are violet to reddish blue. They are advantageously used as basic dyes, in particular for coloring paper. The dyes show substantial affinity and, applied from an aqueous dyeing medium, give substantial degrees of exhaustion;

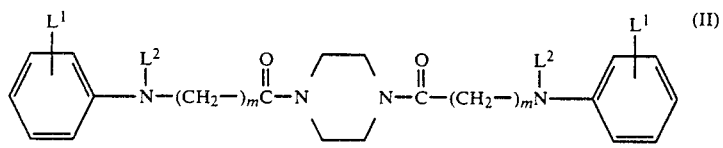

where each $L^1$ is identical or different, being independently of the other hydrogen, $C_1$-$C_4$-alkyl, $C_1$-$C_4$-alkoxy or halogen, $L^2$ is identical or different, being independently of the other hydrogen or $C_1$-$C_4$-alkyl, and m is identical or different, being 1 or 2, with the proviso that, if $L^2$ is the same in both cases with each $L^2$ being hydrogen, methyl or ethyl and if each m is 1, then $L^1$ is not hydrogen in both cases and that, if $L^2$ is hydrogen in both cases and each m is 1, then $L^1$ is not ortho-disposed chlorine in both cases.

Those compounds of the formula II which are excluded by the definition are known and described in J.

they are therefore very environment-friendly.

The Examples which follow further illustrate the invention.

EXAMPLE 1

12 g of 1,4-bis(chloroacetyl)piperazine and 2.5 g of magnesium oxide were heated to 90° C. in 50 ml of water and admixed with 14.8 g of N-ethyl-3-methylaniline in the course of an hour. After heating at 100° C. for four hours, the mixture was diluted with 100 ml of water and adjusted to pH 3–3.5 with conc. hydrochloric acid. After cooling down to room temperature, the crystalline product of the formula

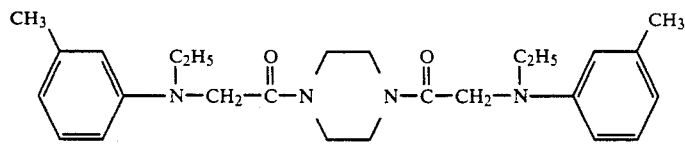

was filtered off with suction, washed with 175 ml of water and dried. Yield: 20 g; melting point 217–220° C.

EXAMPLE 2

408 g of 1,4-bis(N-phenyl-N-ethylaminoacetyl)-piperazine and 508 g of bis(n,N-dimethylaminophenyl)methane were heated in 1,500 g of glacial acetic acid and 300 g of 1,2-propylene glycol at 100° C. for 10 minutes and then cooled back to 44–46° C. (This temperature was maintained during the remaining reaction time). Following addition of 10 g of chloranil and 10 g of the iron complex of dibenzotetraaza[14]annulene, air was passed through the solution at a rate of 200 l/h for 8 hours with vigorous stirring. Filtration gave 2,198 g of an approximately 38% strength by weight solution of the dye of the formula

EXAMPLE 3

44 g of the product described in Example 1 and 59 g of bis(4-ethylamino-3-methylphenyl)methane in 200 l of glacial acetic acid and 40 g of 1,2-propylene glycol were initially briefly heated to 95°–100° C. and then cooled back to 44–46° C. (This temperature was maintained during the remaining reaction time). Following the addition of 1 g of choranil and 1 g of the iron complex of dibenzotetraaza[14]annulene, the solution was vigorously stirred under oxygen (approximately 50 mb hydrostatic overpressure) for 1 hour, during which 4.6 of oxygen were absorbed. Filtration gave 305 g of an approximately 31% strength by weight solution of the dye of the formula

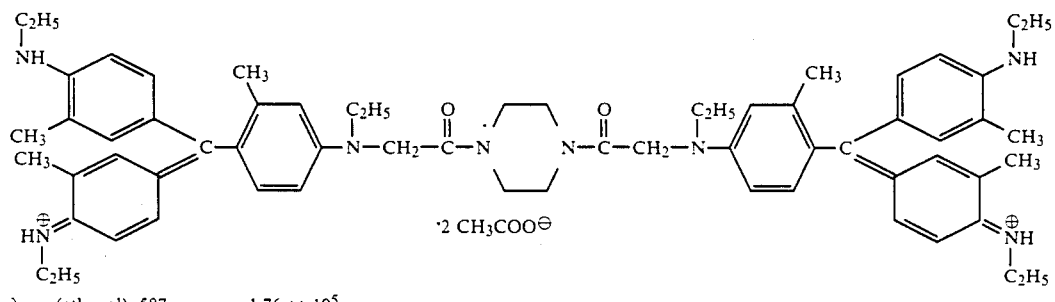

$\lambda_{max}$ (ethanol): 587 nm, $\epsilon = 1.76 \times 10^5$.

The same method is used to obtain the dyes of the formula

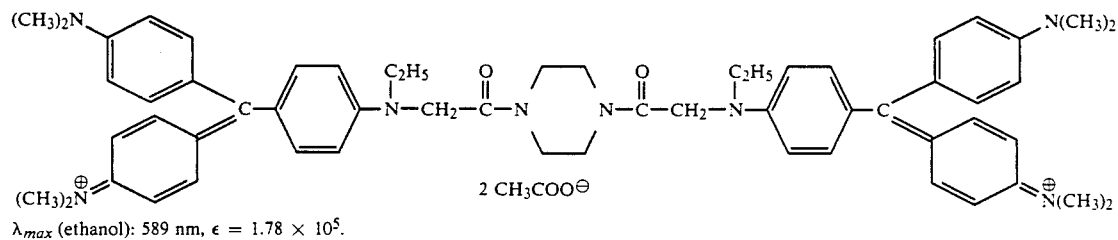

$\lambda_{max}$ (ethanol): 589 nm, $\epsilon = 1.78 \times 10^5$.

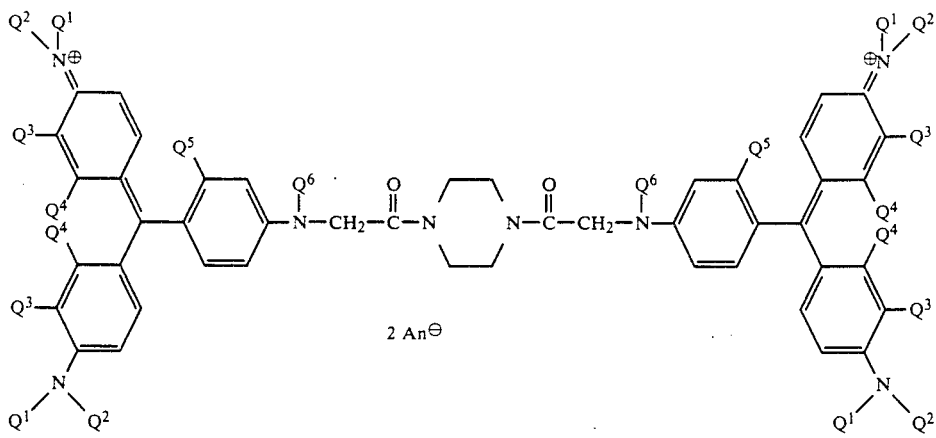

listed in the table below.

| Ex. No. | $Q^1$ | $Q^2$ | $Q^3$ | $Q^4$ | $Q^5$ | $Q^6$ | $An^\ominus$ |
|---|---|---|---|---|---|---|---|
| 4 | $CH_3$ | $CH_3$ | H | H | $CH_3$ | | $CH_3COO^\ominus$ |
| 5 | $C_2H_5$ | H | $CH_3$ | H | H | | $CH_3COO^\ominus$ |
| 6 | $CH_3$ | $C_2H_5$ | H | H | H | | $CH_3COO^\ominus$ |
| 7 | $C_2H_5$ | $C_2H_5$ | H | OH | H | | $CH_3COO^\ominus$ |
| 8 | $C_2H_5$ | $C_2H_5$ | H | $OCH_3$ | H | | $CH_3COO^\ominus$ |
| 9 | $C_2H_5$ | $C_2H_5$ | H | $CH_3$ | H | | $CH_3COO^\ominus$ |
| 10 | $C_2H_4CN$ | $CH_3$ | H | H | H | | $CH_3COO^\ominus$ |
| 11 | $C_2H_4Cl$ | $CH_3$ | H | H | H | | $CH_3COO^\ominus$ |
| 12 | $C_2H_4OH$ | $CH_3$ | H | H | H | | $CH_3COO^\ominus$ |
| 13 | $C_2H_4OH$ | $CH_3$ | H | H | $CH_3$ | | $CH_3COO^\ominus$ |

We claim:
1. A triphenylmethane dye of the formula I

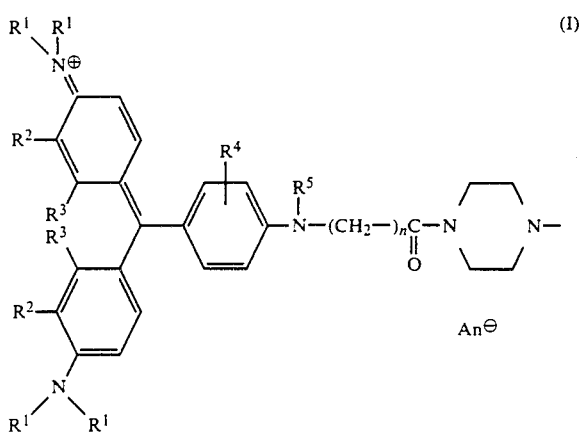

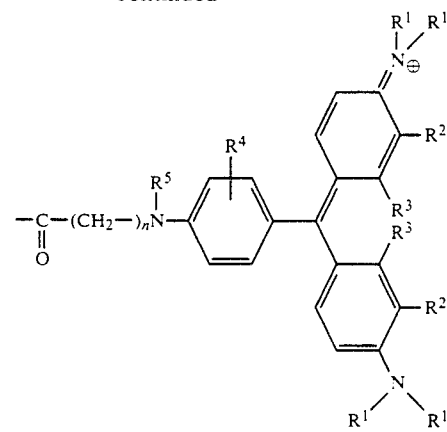

where each
$R^1$ is identical of different, being independently of the others hydrogen, $C_1$-$C_6$- alkyl, or $C_1$-$C_6$-alkanoyloxy, $C_1$-$C_4$-alkoxycarbonyl, cyano, chlorine acetyl, acetylamino or phenyl, or two $R^1$ radicals together with the nitrogen atom joining them form a saturated 5- or 6-membered heterocyclic raidcal selected from the group consisting of pyrrolidino, piperidino, morpholino, thiomorpholino, piperazino and N-($C_1$-$C_4$-alkyl)piperazino,
$R^2$ and $R^5$ is identical or different, being independenlty of the others hydrogen or $C_1$-$C_4$-alkyl,
$R^3$ and $R^4$ is identical or different, being independently of the others hydrogen, $C_1$-$C_4$-alkyl, $C_1$-$C_4$-alkoxy or halogen,
$An^\ominus$ is one equivalent of an anion, and
n is identical or different, being 1 or 2.

2. A triphenylmethane dye as claimed in claim 1, wherein each
$R^1$ is independently of the others hydrogen, $C_1$-$C_4$-alkyl or 2-hydroxyethyl,
$R^2$ is independently of the others hydrogen or methyl,
$R^3$ and $R^4$ is independently of the others hydrogen, methyl, methoxy, ethoxy or halogen, and
$R^5$ is independently of the other hydrogen or $C_1$-$C_4$-alkyl, and $An^\ominus$ and n are each as defined in claim 1.

* * * * *